United States Patent [19]

Gillespie

[11] 4,211,750
[45] Jul. 8, 1980

[54] BRUSH AND DEODORANT HOLDER

[76] Inventor: Dorie Gillespie, 507 E. Taber, Fort Wayne, Ind. 46803

[21] Appl. No.: 8,593

[22] Filed: Feb. 1, 1979

[51] Int. Cl.² .......................... A61L 3/00; A61L 9/04
[52] U.S. Cl. ................................. 422/123; 206/361; 211/65; 239/34; 248/110; 312/31; 312/206; 422/4; 422/5; 422/300
[58] Field of Search .............. 422/292, 300, 293, 301, 422/4, 28, 120, 123, 5; 211/65, 66; 248/110; 206/361; 312/206, 31; 239/34, 57, 60, 289; 312/31.01, 31.02, 31.2; 220/87

[56] References Cited

U.S. PATENT DOCUMENTS

| | | | |
|---|---|---|---|
| 1,215,294 | 2/1917 | Macdonald | 312/206 |
| 1,224,696 | 5/1917 | Wise | 312/205 UX |
| 1,361,842 | 12/1920 | Evslin | 312/206 X |
| 1,419,593 | 6/1922 | Thompson | 312/206 X |
| 1,565,684 | 12/1925 | Thesee | 312/206 UX |
| 1,579,958 | 4/1926 | Schwartz | 312/206 UX |
| 2,099,339 | 11/1937 | Hart | 422/300 |
| 2,464,085 | 3/1949 | Hess | 206/361 |
| 2,472,683 | 6/1949 | Richardson | 312/31.1 |
| 3,085,678 | 4/1963 | Moore | 206/361 |
| 3,361,507 | 1/1968 | O'Neil | 312/206 |
| 3,724,002 | 4/1973 | Buck, Jr. | 4/222 |
| 3,910,495 | 10/1975 | Cummings et al. | 239/60 X |
| 4,096,994 | 6/1978 | Brysan | 239/57 |

FOREIGN PATENT DOCUMENTS 592363 10/1925 France ....................... 422/300

*Primary Examiner*—Joseph Scovronek
*Assistant Examiner*—Roger F. Phillips
*Attorney, Agent, or Firm*—Gust, Irish, Jeffers & Hoffman

[57] ABSTRACT

A toilet brush and deodorant holder has a base and a child-proof, removable, elongated, upright cylindrical column supported thereon. The column comprises inner and outer concentric walls radially spaced from one another to define an elongated, annular, compartmented passage therebetween. The base contains a vented cavity for holding a deodorant cake. Vapors from the cake flow upwardly through the annular passage to the upper ends of the concentric walls. A cap is removably supported at the upper ends of the walls and has vents in registration with the annular passage. The cap has a central opening for supporting the handle of a toilet brush which is insertable for storage in the cylindrical chamber defined by the inner wall. The brush is supported in spaced relation from the cake by the lower portion of the inner wall which has an aperture to permit drainage of moisture from the brush onto the cake.

6 Claims, 5 Drawing Figures

BRUSH AND DEODORANT HOLDER

BACKGROUND OF THE INVENTION

1. Field of the Invention

This invention relates to toilet area deodorant containers and brush holders, and more particularly to those holders which are floor mounted in an area adjacent the toilet bowl with which the brush is used.

2. Description of the Prior Art

Toilet brush holders are well known in the art, as are toilet area deodorant holders. In prior devices, separate containers were used to support the toilet brush and the deodorant. Thus two separate containers were required with separate areas for placement of the containers; those containers were often of contrasting or conflicting style and decor having a non-appealing aesthetic appearance. Further, the deodorant container, being smaller in size, was susceptible to child manipulation and access thereby providing an attractive nuisance to infants and children.

SUMMARY OF THE INVENTION

A base, preferably constructed of a suitable plastic material, is vented adjacent its lower end and supports an elongated, upstanding cylindrical column. The base has a cavity for receiving an air freshner or deodorant cake therein. The base cavity has a cake support with openings therein being in communication with base vents formed below the support. The column comprises inner and outer concentric walls defining an annular passage therebetween. The base and lower column end are provided with child-proof safety closure threads having locking detents and spaces to prevent removal by simple unscrewing rotation.

The inner wall defines an elongated cylindrical chamber for receiving a toilet brush having an elongated handle, and is funneled at its lower end to support the brush, the funnel apex having an opening directly above the deodorant cake to permit moisture drainage from the brush onto the cake aiding deodorant release. The outer surface of the funnel captures and directs the deodorant vapors to the annular passage. A cap is provided for removable retention by the upper portion of the column and is provided with a central opening for insertion over the brush handle. Vents are provided in the cap in registration with the annular passage to provide escape to the ambient air of the deodorant vapors.

Thus, a single container is provided for a toilet brush as well as for a deodorant cake, with a construction wherein the moisture from a recently used brush is utilized in a beneficial and advantageous manner by aiding in deodorant release. Further, while the deodorant cake is located near floor level, passages are provided which release the vapor to the ambient air at a level substantially above floor level providing for more effective deodorant use.

Therefore, it is an object of this invention to provide a combination toilet brush and deodorant container.

A further object to to provide a toilet brush and deodorant container wherein moisture from the toilet brush is used to aid in deodorant vaporization.

A still further object of this invention is to provide a toilet brush and deodorant container having a child-proof safety release for the deodorant container.

Another object of this invention is to provide in the container of the above objects a tray or cavity for supporting the deodorant cake near floor level but releasing deodorant vapors substantially above floor level.

The above-mentioned and other features and objects of this invention and the manner of attaining them will become more apparent and the invention itself will be best understood by reference to the following description of an embodiment of the invention taken in conjunction with the accompanying drawings.

DESCRIPTION OF THE PREFERRED EMBODIMENT

Figure 1:
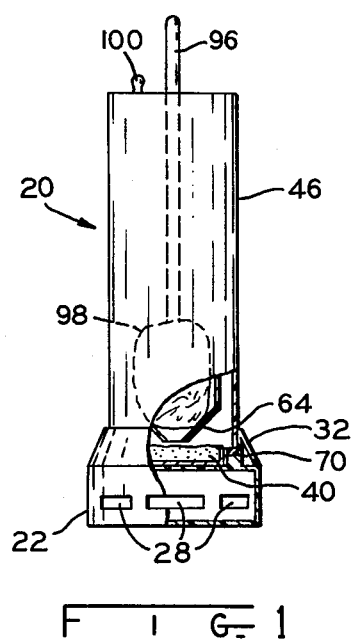
FIG. 1 is a side, elevational view, partially broken away, of an assembled preferred embodiment of the invention.
Figure 2:
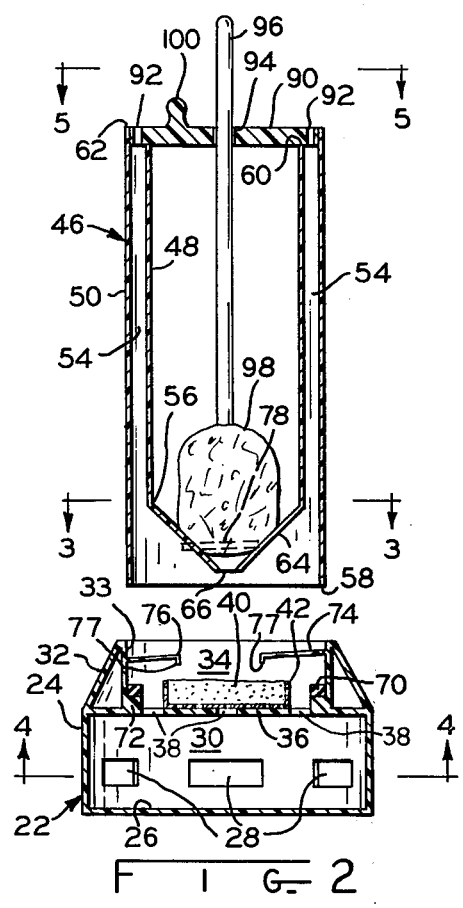
FIG. 2 is a longitudinally section, exploded view of the embodiment of FIG. 1.

Referring to the drawings, toilet brush and deodorant holder, generally indicated at 20, has cylindrical base 22 with side wall 24 and bottom wall 26 defining cylindrical space 30. Wall 24 has a plurality of vent openings 28 formed circumferentially therein adjacent bottom 26. Supported on wall 24, and molded integrally therewith, is conical or tapered section 32 having cylindrical inner wall 33 defining cavity 34. Section 32 has support or floor 36 having a plurality of openings 38 formed therein to provide communication with cavity 30 and openings 28. Floor 36 also provides support for deodorant or air freshner cake 40 which may be provided with a perforated tray 42.

Figure 3:
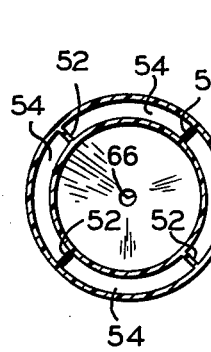
FIG. 3 is a section taken at 3—3 in FIG. 2.
Figure 4:
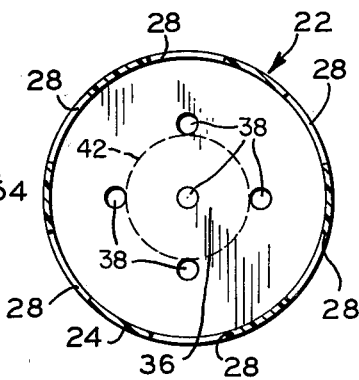
FIG. 4 is a section taken at 4—4 in FIG. 2.

Elongated hollow cylindrical column 46 is provided having inner cylindrical wall 48 and concentric outer cylindrical wall 50 radially spaced therefrom by elongated radial vanes 52 which are affixed on their respective inner longitudinal edges to wall 48 and on their respective outer longitudinal edges to wall 50. Thus, a plurality of longitudinal passages 54 (FIG. 3) is formed from lower edge 56 of wall 48, which is spaced upwardly from the lower edge 58 of wall 50, to the upper edge 60 of wall 48 which is spaced slightly downwardly from the upper edge 62 of wall 50.

Funnel 64 has its upper peripheral edge joined or affixed to lower edge 56 of wall 48 and has opening 66 at its lower end which, when the outer wall 50 is inserted in cavity 34 of base 22, is spaced slightly above cake 40 in its supported position on floor 36 of cavity 34. An annular upwardly diverging passage is thus formed between the outer surface of funnel 64 and the inner surface of wall 50, defining an annular space of decreasing cross section in the vertically upward direction which maximizes capture of the deodorant vapors from cake 40 and concentrates the upward flow into passages 54.

Resilient ring 70 is place on annular ledge 72 formed on, and extending inwardly from, inner wall 33 of base 22. Bottom edge 58 of outer wall 50 is urged against ring 70 during assembly of column 46 into base 22. Threads 74, having elongated openings 76 therebetween, are formed on inner wall 33. Shoulders 77 are formed on either side of openings 76. Openings 76 register respectively with elongated thread portions 78 formed on the outer surface of the lower portion of wall 50. Portions 78 have a length slightly less than the length of openings 76 and are registrable with respective openings 76. Column 46 is inserted into base cavity 34 with portions 78 in registry with openings 76 until edge 58 engages ring 70. In assembly, column 46 is depressed against ring 70 until portions 78 are below shoulders 77, and is then rotated in a clockwise screwing direction until portions 78 clear shoulders 77 after which column 46 is released. To disassemble holder 20, column 46 is depressed against ring 70 until portions 78 are below shoulders 77 and is then rotated in a counterclockwise direction until portions 78 register with openings 76 and is finally lifted clear of base 22. In this manner, a safety lock is provided which will inhibit opening of the device by infants or children. The particular safety lock employed is not my invention and it is to be understood other safety locks well known in the art may be employed.

Figure 5:
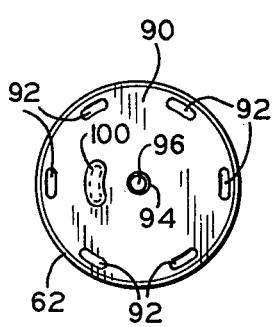
FIG. 5 is a top plan view of the embodiment shown in FIG. 1, as viewed at 5—5.

Upper end 62 of wall 50 extends slightly above upper edge 60 of inner wall 48 to provide a recessed holding support for circular cap 90 which is received within upper end 62. Cap 90 has arcuate vents 92 formed at the outer periphery thereof (FIG. 5) and are respectively in registration with passages 54 to form communication between passages 54 and the ambient air. Central opening 94 is formed in cap 90 for receiving elongated handle 96 of brush 98. Handle 100 may be formed on the upper surface of cap 90 to provide for manual removal and insertion of cap 90 in column 46. All of the parts heretofore described may be advantageously made of molded plastic material which is corrosion resistant, may be aesthetically colored and designed, is breakage resistant, and relatively inexpensive to manufacture.

In operation of the embodiment shown, column 46 is removed from base 22 by exerting a downward pressure and at the same time unscrewing it relative to base 22 to effect removal therefrom. A deodorant or air freshner cake 40 is placed on floor 36 of base 22, and member 46 may then be reattached by a downward screwing rotative pressure; this provides an effective child-proof fastening to prevent access to cake 40. Cap 90 is removed, as by lifting with handle 100, and brush 98 is inserted in the chamber formed by wall 48. Cap 90 is then replaced with opening 94 being aligned with handle 96, handle 96 being inserted therethrough, until cap 90 is seated on upper edge 60. Moisture in brush 98 drips on and flows downwardly along the walls of funnel 64 and exits opening 6 6 onto cake 40 aiding in deodorant vaporization. Vapors from cake 40 are captured by the outer surface of funnel 64 and the inner surface of wall 50 and convergently flow upwardly between walls 50 and 48 in passages 54. The upward flow continues to the upper end of member 46 and outwardly from vents 92 to the ambient air. Ambient air flows through the vents 28 in base 22, openings 38 in floor 36 and around cake 40 to carry the deodorant vapors upwardly.

When is is desired to use brush 98 for cleaning purposes, cap 90 may be removed by lifting handle 100, and the brush removed from column 46. Thus, a single container is used for both deodorant and brush holding functions with the brush moisture being used to aid in the vaporization of the deodorant cake and with a vapor capture flow path causing the vapors to be released to ambient air at a relatively elevated level, the deodorant cake being placed adjacent the floor level. The deodorant cake is effectively hidden from view and attachment to the toilet bowl or tank is unnecessary.

While there have been described above the principles of this invention in connection with specific apparatus, it is to be clearly understood that this description is made only by way of example and not as a limitation to the scope of the invention.

What is claimed is:

1. A brush and deodorant holder comprising a base, a wall defining an elongated chamber for receiving the brush, said chamber having a lower end removably supported by said base in upwardly extending relation therefrom, said base having a cavity therein for receiving an air freshner substance; the lower end of said chamber having an opening therein providing communication between said cavity and said chamber; passage means on said wall for providing a contained vapor flow exteriorly of said chamber from said cavity to the upper portion of said wall; and a cap removably supported on said wall at the upper end of said chamber and having an opening therein for receiving and supporting a brush handle, said cap having vent openings in communication with said passage means; said base having vent openings in communication with said cavity whereby a flow path is provided for ambient air through said base vent openings to said cavity, through said passage means, and outwardly through said cap vent openings.

2. The apparatus of claim 1 wherein said passage means comprises a second wall supported in laterally outwardly spaced relation to said first-named wall to define an elongated passage for communication from said cavity to said cap.

3. The apparatus of claim 2 wherein said first-named wall is funneled inwardly at the lower end thereof to an opening at the apex thereof to support a brush and to provide said communication from said chamber to said cavity thereby to drain water from said brush onto said substance, said funneled end of said first wall and said second wall defining a relatively large capture area for deodorant vapors from said substance.

4. The apparatus of claim 2 wherein said first and second walls are cylindrically shaped; said second wall is substantially parallel to and laterally and outwardly spaced from said first wall to define said passage therebetween, said passage being in communication at its upper end with said cap vent openings and in communication at its lower end with said cavity thereby to provide for vapor passage to and vapor dissemination from the upper end of said passage means.

5. The apparatus of claim 4 including safety fastening means removably connecting said chamber lower end to said base for inhibiting child-removal of said chamber from said base.

6. The apparatus of claim 5 wherein said base comprises a cylindrical wall; said cavity having a floor for supporting said substance; openings being formed in said floor; said base vent openings comprising circumferentially elongated slots formed in said base wall below said cavity floor to provide for communication between ambient air and said cavity floor openings; and a plurality of spaced, elongated vertical vanes each attached to and extending between said first and second walls to provide said laterally spaced relationship therebetween.

* * * * *